United States Patent [19]

Ehrenfeld

[11] Patent Number: 4,590,060

[45] Date of Patent: May 20, 1986

[54] AGENT FACILITATING LIPOSOME CELLULAR WALL TRANSPORT, A METHOD FOR THE PRODUCTION THEREOF AND ITS USE

[76] Inventor: Udo Ehrenfeld, Furtmayrstrasse 20, 8400 Regensburg, Fed. Rep. of Germany

[21] Appl. No.: 557,738

[22] Filed: Dec. 2, 1983

[30] Foreign Application Priority Data

Sep. 26, 1983 [DE] Fed. Rep. of Germany ....... 3334751
Oct. 7, 1983 [DE] Fed. Rep. of Germany ....... 3336583

[51] Int. Cl.$^4$ ..................... A61K 43/00; A61K 49/00
[52] U.S. Cl. .......................................... 424/1.1; 424/9; 422/61; 568/449; 568/471
[58] Field of Search ................. 568/449, 471; 424/1.1, 424/9; 422/61

[56] References Cited

U.S. PATENT DOCUMENTS

| | | | |
|---|---|---|---|
| 4,157,323 | 6/1979 | Yen et al. | 424/1.1 |
| 4,280,011 | 7/1981 | DeSimone | 568/449 |
| 4,310,505 | 1/1982 | Baldeschwieler et al. | 424/1.1 |
| 4,329,332 | 5/1982 | Couvreur et al. | 424/1.1 |
| 4,377,567 | 3/1983 | Geho | 424/1.1 |
| 4,429,008 | 1/1984 | Martin et al. | 424/1.1 |
| 4,460,560 | 7/1984 | Tökes et al. | 424/1.1 |

FOREIGN PATENT DOCUMENTS

3383 10/1983 World Int. Prop. O. ............ 424/1.1

OTHER PUBLICATIONS

Van Linde et al, Chemical Abstracts, vol. 88 (1978) #61784.
Merck Index, 8th Ed., Eds. Stecher et al, Merck & Co. Inc., Rahway, N.J., 1968, pp. 1094–1095.
Ritter et al, Cancer Research, 41 (1981), 2366-71.

*Primary Examiner*—Christine M. Nucker
*Attorney, Agent, or Firm*—Ostrolenk, Faber, Gerb & Soffen

[57] ABSTRACT

An agent is described in which contains an aldehyde of formula I $$RCHO \qquad (I)$$

in which R is a hydrogen atom, a straight-chain or branched hydrocarbon group having 1 to 4 carbon atoms, and preferably an alcohol of formula II $$R'CH_2OH \qquad (II)$$

in which R' has the meaning indicated above. The agent is used together with charged liposomes. By the administration of the agent, the permeability of the liposomes through tissue cell walls is substantially improved and tagged liposomes accumulate around and in a malignant tumor. A kit for use in diagnosis and therapy is also described.

26 Claims, No Drawings

AGENT FACILITATING LIPOSOME CELLULAR WALL TRANSPORT, A METHOD FOR THE PRODUCTION THEREOF AND ITS USE

BACKGROUND OF THE INVENTION

The present invention relates to an agent and kit for use in connection with the diagnosis and therapy of malignant tumors, a method for the production thereof and its use, as well as the use of charged liposomes for the diagnosis and therapy of malignant tumors.

It has been known for quite some time that D- and L-glycerinaldehydes can be effectively used against ascitic tumors in mice [O. Warburg, K. Galveka, A. Gessler and S. Lorenz, Z. Klin. Chem. 1, 175 (1963)]. In accordance therewith, the formation of cancer which is caused by intraperitoneally injected ascites tumor cells in mice can be prevented if, at the same time or on the next day, D- or L-glycerinaldehyde is also administered intraperitoneally. Compounds such as 2-oxopropanol (pyruvaldehyde) [Apple and Greenberg, Cancer Chemotherpaie, 52, 687 (1968); Neoplasma 24, 210 (1970)] as well as acrolein [K. Motycka and L. Lacko, Z. Krebsforschung 66, 491 (1965)] were also effective, although to different extents.

Glycerinaldehyde is a metabolic product and its inhibiting effect on the development of cancer cells has been ascribed to the fact that it apparently impedes the glycolysis [Skamoto, A. and Prasad, K.N.: Cancer Research, 32, 532 (1972)] which is used by cancer cells to a substantial extent as an energy-delivering process. Doses of glycose and insulin accelerate the growth of certain tumors by 8.3 times [Gaison, T. C., Legros, N. and Geimann, R.: Cancer Research 32, 233 (1972)]. It has, however, been found [B. Mendel, Klin. Wschr. 8, 169 (1929)], that only the L-form of glycerinaldehyde is effective as glycolysis inhibitor, for instance, in the case of so-called Jensen's sarcoma while the D-form is not, but, on the other hand, the D-form otherwise has stronger cancerotoxic action than the L-form [O. Warburg, K. Gálveka, A. Gessler and S. Lorenz, Z. Klin. Chem. 1, 175 (1963)].

Studies on inhibiting of the incorporation of C labeled nucleosides in DNA and RNA also showed that D-glycerinaldehyde strongly impedes (aerobically and anaerobically) the incorporation of $^{14}C$-thymine into DNA, while L-glycerinaldehyde, although it impedes anaerobically, impedes aerobically only to a slight extent. This shows that there is evidently still some other possibility, aside from the inhibition of glycolysis, for the action of glycerinaldehyde.

Solid tumors are not affected by glycerinaldehyde [N. Brock and P. Neikamp, Z. Krebsforschung 67, 93 (1965)], even if the glycerinaldehyde is administered intravenously, intratumorally or intra-arterially. The authors arrive at the conclusion that glycerinaldehyde cannot be used for the chemotherapy of tumors.

It has also been proposed to increase the concentration of glycerinaldehyde in the animal or human to such an extent that the rapid degradation of the glycerinaldehyde can be counteracted with sufficient assurance and that therefore effects could be expected. Practical tests on this, to be sure, are lacking since such proof could be given only with the use of an artificial kidney [M. v. Ardenne, Naturwiss. 51, 217 (1964)].

U. Ehrenfeld [Krebsgeschehen 5, 132 et seq. (1979)] has reported on the cancerotoxic effect of a mixture of acetaldehyde and ethanol. The mixture contains 3 to 10 g acetaldehyde per 1000 g of ethanol. It was found, however, that the effect of this mixture in the treatment of solid malignant tumors as well as of metastases is insufficient.

Intravenously employed liposomes as carriers of markers and medication are not able to pass through continuous capillary walls; they are, to be sure, taken up rapidly by phagocyting cells [G. Poste, Biol. of the Cell, 47, 19 (1983); F. H. Roerdink, J. Dijkstra, G. Hartman, B. Bolscher and G. Scheephof, Biochem. Biophys. Acta 677, 79 (1981); R. M. Ahra and C. A. Hunt, Biochem. Biophys. Acta 666, 493; C. Nicolau, A. Le Pape, Ph. Soriano, F. Fargette and M.-F. Intrel, Proc. Natl. Acad. Sci. USA 80, 1068 (1983)]. This inability on their part to leave the circulation system has been documented with sufficient certainty [B. E. Ryman, G. M. Barrat, R. H. J. Regent, Biol. of the Cell, 47, 71 (1983); M. Bundgaard, Ann. Rev. Physiol. 42, 325 (1980)], which proved them to be unsuitable for use as direct carriers of markers or medication to or into tumors (V. J. Richardson, B. E. Ryman, R. F. Jewkes, K. Jeyasingh, M. H. N. Tattersal, E. S. Newlands and S. B. Kaye, Br. J. Cancer, 40, 35 (1979)]. A simple administration of liposomes by inhalation failed as a result of the fact that the alveola wall of the lung could not be penetrated by the liposomes within a passage time sufficient for therapy or in case of different administration tissue walls which could correspondingly not be penetrated.

The access path which Poste and Fidler use [G. Poste, R. Kirsch, W. Fogler and I. J. Fidler, Cancer Res. 39, 881 (1979); G. Poste and R. Kirsch, Cancer Res. 39, 2582 (1979); I. J. Fidler, A. Raz, W. E. Fogler, R. Kirsch, P. Bugelski and G. Poste, Cancer Res. 40, 4460 (1980); I. J. Fidler, Z. Barnes, W. E. Fogler, R. Kirsch, P. Bugelski and G. Poste, Cancer Res. 42, 496 (1982)] by intravenously injecting liposomes which contain immune modulators in aqueous phase appears very successful in animals. These liposomes are taken up by monocytes in the blood path which become alveolar macrophages in the lung and as such are activated by the molecules of the immune modulator. They contribute significantly to the control of pulmonary metastases. Because of the above-mentioned inability of the liposomes to leave the circulation without the help of cells, this method, however, could not be employed up to now for diagnosis and therapy in humans.

There is a great need for an agent which is able to improve the passage of liposomes through cellular walls, such as, for instance, the cell walls of the lung, of the blood vessels, of the lymph vesssels, etc., so that the liposomes are able to arrive at the place where they could develop their action when they were charged with medicaments.

The diagnosis of malignant tumors is frequently extremely difficult. Malignant tumors can only be detected by x-ray after they have reached a given size. The formation of small tumors and metastases can frequently not be detected, with the result that malignant tumors frequently can only be incompletely removed upon surgery. Therefore, there is a need for a method of diagnosis by which even small tumors can be detected and recognized in simple and easy manner.

The object of the present invention is therefore to make available an agent and its use in connection with the diagnosis and treatment of malignant tumors, the agent being capable of being produced in simple manner, relatively non-toxic for the patient who is to be treated and not imposing without excessive strain on the body.

It has now surprisingly been found that certain aldehydes of the type described below are able, in higher doses, to effect a direct passage of liposomes through cell walls, particularly the walls of pulmonary alveoli and lymph and blood capillaries. In this way, there is made possible a new method of detecting and a new manner of treating malignant tumors, since the liposomes charged with marker and/or medicament pass directly to the malignant tumor and carry out the greatest possible action there directly for the detection and treatment of the tumor.

The objects of the invention are achieved by the employment of an agent in connection with the diagnosis and therapy of tumors which is characterized by the fact that, in addition to ordinary excipients and/or diluents, it contains an aldehyde of formula I $$RCHO \quad (I)$$

in which R is a hydrogen atom or a straight-chain or branched hydrocarbon group having 1 to 4 carbon atoms, in which connection the free aldehyde may also be liberated metabolically directly or indirectly by substances. A preferred agent in addition to the aldehyde contains an alcohol of formula II $$R'CH_2OH \quad (II)$$

in which R' has the meaning indicated above for R.

The invention furthermore relates to a use of the above-mentioned agent for the diagnosis and control of malignant tumors which is characterized by the fact that the use is effected together with charged liposomes. Surprisingly it has been found that the agent of the invention substantially improves the permeability of cell walls for charged liposomes.

The above-indicated article by U. Ehrenfeld does not disclose that an agent which contains ethanol and acetaldehyde improves the permeability of cell walls for charged liposomes. This was surprising and was not obvious. By the administration of the agent in accordance with the invention, followed by administration of charged liposomes it is possible, in simple manner, to diagnose and treat tumors.

The invention furthermore concerns the use of charged liposomes for the diagnosis and control of malignant tumors together with the above-mentioned agent.

The pharmaceutical agent of the invention may contain the aldehyde as such in ordinary pharmacologically compatible excipients and/or diluent. It is particularly preferred to use the aldehyde in aqueous and/or alcoholic solution. In accordance with the invention, it is particularly preferred to use the aldehyde in question together with its corresponding alcohol.

Preferred agents indirectly or directly liberate and/or contain formaldehyde/methanol, acetaldehyde/ethanol, n-propionaldehyde/n-propanol, isopropionaldehyde/isopropanol, n-butyraldehyde/n-butanol, isobutyraldehyde/isobutanol, tert.butyraldehyde/tert.-butanol, n-valeraldehyde/n-pentanol or mixtures of these compounds.

An optimum effect of the new pharmaceutical preparation, i.e. an improvement in the permeability for charged liposomes, is obviously only obtained if the concentration of the aldehyde in the body can be maintained high for long periods of time, and preferably uniformly high. It is known that ethanol is degraded to acetaldehyde in the human body, the rate of degradation of the ethanol above a given concentration, in the same way as that of the acetaldehyde being practically independent of the concentration and the rate of degradation of the acetaldehyde being evidently of the same magnitude or somewhat less than that of the ethanol. The concentration of acetaldehyde which occurs upon the natural degradation of alcohol is, however, clearly not high enough.

By the agent according to the invention it is possible, on the one hand, to develop within the body of a patient suffering from the tumors and/or metastases a sufficiently high concentration of a product of metabolish—e.g. acetaldehyde—which, as agent for the detection of malignant tumors, has anti-tumor activity in its action in improving the passage of liposomes through cells and tissues. In the preferred embodiment of the invention, there is a simultaneous administration of a substance which is as harmless as possible—in particular the corresponding alcohol—which continuously degrades to the substance active as agent for detecting malignant tumors which has anti-tumor activity in its effect of improving the penetration of liposomes through the cells and tissues.

The acetaldehyde/ethanol pair is practically non-toxic: it can be administered in suitably high doses. From this there results the possibility of continuous treatment, even in combination with radiation treatment. The immunobiological system is subjected to a positive influence, and combination with other medicaments as well as with surgical and radiological measures is possible.

In addition to the ethanol/acetaldehyde mixture other analogous mixtures of the above-mentioned type are also fundamentally possible, such a methanol/formaldehyde, propanol/propanal, butanol/butanal, etc. Methanol is degraded substantially more slowly in the human body than ethanol, and propanol is degraded two times faster than ethanol. The pair must be chosen to be suitably non-toxic. For example, as is known, the pair methanol/formaldehyde is toxic, which must be taken into consideration upon medication. Which pair is the most favorable in the individual case or whether combinations are to be used depends on the individual case and can easily be determined by the physician.

The pharmaceutical agent of the invention may, in each case, contain only a single specifically selected aldehyde as well as mixtures of aldehydes. Acetaldehyde is a particularly preferred aldehyde. It is particularly preferred, in turn, to use it together with ethanol.

The use of the aldehydes is not necessarily coupled with the presence of the corresponding alcohols. Aqueous solutions of the aldehydes can also be used. Instead of the free aldehydes, one may also employ in accordance with the invention aldehyde derivatives which form the free aldehyde in the metabolism of the patient treated with the pharmaceutical agent of the invention. Suitable aldehyde derivatives are, for instance, the acetals or semi-acetals or condensation products, which may also be used as such or in dissolved form (water or alcohols) as well as in the mixtures with the aldehydes and/or alcohols.

In another preferred embodiment of the invention, the agent contains small amounts (less than 0.05 wt.%) of peroxides, especially $H_2O_2$ and/or aldehyde peroxide or hydroxy hydroperoxide as well as the peroxide of the corresponding carboxylic acid. The action of the liposomes is further improved by the content of peroxides.

The concentration of aldehyde in the preparation according to the invention is determined, on the one hand, by its compatibility and, on the other hand, by the dose to be administered. For the pair ethanol/acetaldehyde, an acetaldehyde concentration in the alcohol of less than $2 \times 10^{-4}$ mole/liter is frequently unsatisfactorily slow in its action. The action increases with an increase in the concentration of aldehyde and its upper limit is formed in the individual case, as a rule, by incompatibility of the acetaldehyde which may possibly occur. In practice, for instance, ethanol/acetaldehyde solutions with $5 \times 10^{-2}$ mole to 1 mole acetaldehyde per liter of ethanol have proven satisfactory, it being possible to use these mixtures in a dose of, for instance, 10 to 150 cc per day.

It is preferred that the agent contain 11 to 40 g of aldehyde per 1000 g of alcohol, while 15 to 30 g of aldehyde per 1000 g of alcohol is particularly preferred. In general, the agent is diluted with water for administration. The alcoholic solution may be diluted with any amount of water as desired. For example, one volume of the alcoholic solution can be diluted with 1 to 10 volumes and preferably 2 to 5 volumes of water.

The agent of the invention is preferably administered orally in the form of an aqueous solution and drunk by the patient. The agent of the invention can, however, also be administered parenterally, for instance by infusion. The preparation of infusion solutions is well-known to the man skilled in the art and can be effected in a simple manner.

The agent of the invention can be prepared in a simple manner by simply mixing the components. The aldehyde selected is mixed with pharmacologically acceptable excipients and/or diluents, possibly together with the alcohol.

However, it is preferred to prepare the agent of the invention by irradiating an alcohol of formula II

$$R'CH_2OH \qquad (II)$$

in which R' is a hydrogen atom or a straight-chain or branched hydrocarbon group having 1 to 4 carbon atoms with energy-rich radiation, with admission of oxygen.

Gamma radiation, ultraviolet radiation, x-radiation or electron radiation can be employed as energy-rich radiation. The alcohols selected can in this connection be used as such as or alcohol/water mixtures, in which case highly concentrated alcohol/water mixtures may be particularly preferred as starting material. The irradiation is effected with access of oxygen and preferably access of air.

An agent of the invention which is particularly important and effective in practice can be prepared, for instance, by exposing 96% ethanol in the presence of oxygen to energy-rich radiation of the type described until the desired amount of acetaldehyde has been formed. The solution then contains essentially, in addition to a large amount of ethanol, the acetaldehyde together with peroxides such as $H_2O_2$ or acetoperoxide or traces of peracetic acid as well as acetic acid. The last-mentioned substances substantially improve the action of the liposomes.

It has surprisingly been found that, by the preferably oral ingestion of a mixture of the aldehyde of formula I, preferably acetaldehyde, and an alcohol of formula II, preferably ethanol, in aqueous solution, the passage of liposomes from the air into the blood vessels of the lung, and from the blood into the tissue of mammals and particularly of humans, is facilitated and accelerated.

The liposomes are single unilamellar vesicles (SUV) which preferably consist of phosphatidylcholine:phosphatidylserine:cholesterol in a molar ratio of 8:2:10 and are prepared by sonication. Commercially available lipids (Sigma Products), purified by column chromtography can be dissolved in ether, evaporated under $N_2$, suspended again in phosphate—buffered saline solution (PBS)—pH 7.4—and sonicated for 25 minutes at $+2°$ C. with a pulsated Branson 15 sonicator. The sonication is carried out under $N_2$. After the sonication, the liposomes are chromatographed on a Sepharose-4-B column and the fraction of the population with radii less than 300 Å are preferably used [C. Huang, Biochemistry 15, 2362 (1969)]. These liposomes can then be tagged for diagnosis in known manner with preferably 99 m Tc (CEA-France) in accordance with Osborne et al. [M. P. Osborne, V. J. Richardson, K. Jeyasingh and B. E. Ryman, Int. J. Nucl. Med. Biol. 6, 75 (1979)].

In order to check the radioactive labeling, an aliquot portion of the liposomes is then introduced into a Sepharose-4-B column and chromatographed. It is found that the preparation has a specific activity of 99.2% of radioactivity bound to the liposomes and 0.8% free pertechnetate.

Liposomes can be tagged with an appropriate label such as a radioactive tracer or with a dyestuff or both with a dyestuff and radioactive tracer. Such liposomes are particularly suited for diagnosis. The liposomes may furthermore bear a cytostatic, a radioactive radiator, an immune modulator such as, for instance, a muramylic acid dipeptide derivative (MDP) or both a cytostatic and a radioactive radiator or both a radioactive radiator and an immune modulator.

The liposomes can be administered orally and/or parenterally. They are preferably used suspended sterilely in physiological saline solution and administered by inhalation.

In diagnosis, there are generally used liposomes which are tagged with the stain and/or radioactive carrier. For the therapy, liposomes which bear cytostatics, immune modulators and/or radioactive radiators are used. In general, for diagnosis the administration of the agent of the invention is effected on the day before the diagnosis is to be effected. Within a period of 6 to 24 hours after the first administration of the agent of the invention, the agent of the invention is again administered. Thereupon the charged liposomes are administered. The administration of the liposomes is effected preferably about one hour after the last administration of the agent of the invention. It may also be effected directly thereafter or several hours thereafter. It is readily possible for the man skilled in the art to determine the most appropriate dose and the intervals at which the agent of the invention and the liposomes are administered.

For treatment one can proceed, for instance, in the manner that the agent of the invention is administered once to twice a day and then about one hour after administration of the agent, the liposomes are administered, also once or twice a day. This depends on the material carried by the liposomes. It is also possible to administer the agent of the invention and then immediately administer the liposomes.

It was surprising and not obvious that the liposomes collect and accumulate around and in the malignant tumor. A concentrating of the liposomes in reasonable quantity and time around and in the malignant tumor is not possible without the use of the agent according to the invention. It was particularly surprising and not obvious that the liposomes would collect around and within the malignant tumor to such an extent that it becomes possible to treat numerous different tumors and it also becomes possible to detect and diagnose very small tumors in the body of mammals and in particular of humans.

In accordance with the present invention, it is thus possible for the first time to diagnose as well as treat malignant tumors in the case of mammals and particularly in the case of humans in a simple manner without the patient being subjected to stress. Because of the localization of the liposomes as a result of the invention, it is possible to irradiate the tumors in directed fashion nearly without practically any neighboring tissue being damaged and furthermore medicaments, for instance, the cytostatics or immunomodulators, can be brought in accordance with the invention to the place where they actually are to act.

Examples of cytostatics and metastasis inhibitors which can be used in accordance with the invention are all compounds known at the present time as cytostatics and metastasis inhibitors. Examples thereof are melphalan, carmustine, lomustine, cyclophosphamide, estramustine phosphate, iphosphamide, chlorambucil, methrotrexate, pegafur, fluoruracil as well as antibiotics which are used for these purposes.

The visualizing of the Orfan distribution of 99 m Tc labeled liposomes is preferably effected on film with the use of an external gamma camera. An additional or exclusive charging of the liposomes with stain makes it possible in surgical procedures to recognize malignant tumor tissue within healthy tissue. For medicinal treatment of malignant tumors, the liposomes are preferably charged with immunomodulators, for instance muramylic acid dipeptide derivatives, as a result of which there is obtained a clearly detectable reduction in the cancer masses without adverse side effects.

For the treatment of malignant tumors, liposomes—independently of or simultaneously with the medicinal charge—are used as carriers of radioactive substances which—with or without reduction of the deoxygenation in the tissues by suitable agents—are used in and on tumor tissue for radiation with practically exclusive damage to the tumor. During such a treatment, the effect from earlier treatments which has already been obtained can be shown pictorially, for instance, by means of a gamma camera. The radiation treatment is limited by the liposomes to the intended place and the radiation can be individually dosed. Intermediate phases or interruptions in the radiation treatment are utilized by treatment with medicinally charged liposomes which have been preferably charged with immunomodulators. The traditional medicinal cytostatic treatment of malignant tumors is more successful after a treatment with, for instance, ethanol/acetaldehyde and immune-modulator-charged lipsomes than without such prior treatment; a traditional radiation treatment is more successful with such treatment simultaneously and the healthy tissue is protected.

In accordance with a particularly preferred embodiment of the invention, together with the agent of the invention and the liposomes there is administered an agent which increases the deoxygenation in the region of the malignant tumors. In this way, the therapeutic radiation effect is at the same time increased. As agents which increase the deoxygenation in the region of the malignant tumors one can use all agents already known to have this effect. Examples thereof are inositol phosphates (tri-, tetra-, penta-, hexaphosphate) and glycerine phosphate (di- or triphosphates) and other substances which are known to be capable of being incorporated into the heme and possess this effect there.

For exclusive treatment with, for instance, ethanol/acetaldehyde in aqueous solution and immune modulator-charged liposomes (for instance charged with muramylic acid dipeptide derivatives MDP), a malignant tumor mass, for instance melanosarcoma, of a total of 150 g can be treated with good immune reaction of the patient and a period of treatment of half a year if the tumor does not acquire any protective mechanism against the new situation. The immune response in the case treated in this manner is constant with respect to the cell- and tumor-increased reaction of the human organism. Exhaustion of the immune system cannot be observed within the period of time indicated, nor are there any over-reactions or signs of degeneration. The tolerance appears excellent.

In the case of radioactive tagging of the liposomes with a tracer, for instance 99 m Tc, the radioactive radiation is clearly enriched in and around pathogenically degenerated tissue, for instance squamous cell carcinoma or melanosarcoma. Upon elimination of the liberated 99 m Tc, the liposome-bound radioactivity taken up in the cells remains in characterizing manner in the region of the malignant tumors. False-positive results are expected in conditions with local enrichments of macrophages (Tbc, placenta, etc.). By free 99 m Tc, there occured an enrichment of radioactivity, which was eliminatable, in a thyroid adenoma. After the elimination of the free 99 m Tc, there was found a metastasis of a melanosarcoma in this adenoma of the thyroid gland.

Very small amounts of tumor can be displayed precisely. The tumor size of a malignoma is unimportant for the success of the display. The changes of permeability in lung, vessel and cell walls for the liposomes occur after the introduction of aldehyde into organism or its production therein.

By the application of aldehydes, particularly acetaldehyde, without or, strengthened in effect, in combination with immune modulators, preferably cell-wall components, and possibly also their derivatives, encapsulated in liposomes, particularly MDP, there is an increase in the defense to malignant tumors in the bodies of mammals and particularly humans. The breaking down of solid tumors could be observed upon the preferred use of an orally administered mixture of acetaldehyde with ethanol in aqueous solution and of inhalations with liposomes containing muramylic acid dipeptide derivatives effected in timed relationship thereto, for instance 2 hours later. In this case, the acetaldehyde serves to effect a change in the permeability on cell walls.

The passage of liposomes through cell walls (lung/blood, blood-vessel/tissue, lymph vessel/tissue) and the absorption of liposomes in macrophages (monocytes) was facilitated and accelerated. After administration of acetaldehyde, as is known, cross-linking of $NH_2$ groups take place on the cell surfaces and, occasionally, decrease blood sugar level; beta oxidation of fatty acids always occurred. The metabolism products obtained upon the lipolysis act in part similar to acetaldehyde.

An increase in the number of monocytes, of the Rieder forms and of the lymphatic plasma cells in the blood was observed in all the known cases after administration of acetaldehyde. NK and T cells are multiplied and increased in their activity. The production of immunoglobulin is increased. The MDP in liposomes considerably increased the immune reactions known for acetaldehyde, the number, for instance, of monocytes in the blood increased, referred to 4000 leukocytes µl, to more than 20% in the differential white blood count. The activity of the macrophages can, as in known, be increased by estrogens.

The phagocytosis performance of the macrophages upon the destruction of cells of malignant tumors is significantly increased upon the use of acetaldehyde and MDP in the manner indicated. The disappearance of skin metastases and liver metastases and the conversion of lung metastases into aerated structures was noted. A significant macrophage suppuration was found in the histology on the surfaces of malignant tumors. The effect of x-radiation on tumor tissue is improved by macrophage activity. The action of acetaldehyde and liposomes with MDP in the above-indicated manner of use is dependent on quantity; rapidly growing malignant tumors respond better than slowly growing ones. For testing and treatment, a substantially glucose-free and starch-free diet is necessary. Locally, the effect of the active combination is counteracted by glucose, sugar, starch, vitamin C in high doses and vitamin $B_1$ and in general by cortisone and antihistamines.

The effect of the preferred combination of the invention, namely ethanol/acetaldehyde in aqueous solution together with liposomes which are tagged and/or charged with medicaments, preferably immunomodulators, will be explained below, using as example the description of the pathophysiological picture of cancer patients. The differences obtained upon the use of the combination according to the invention for the detection and treatment as compared with the untreated cancer patients can be summarized as follows:

Detection

The tagging concerns malignant tumor tissue.

Treatment (a) Subjective (Evaluation by patient): Freedom from pain, feeding of well-being.

(b) Clinical: At times a slight increase in size, but also a decrease in size of the tumor regions, sometimes within hours and sometimes within days, and in some cases also complete disappearance of tumors and their metastases within months: Restoration of gross strength, normalization of oxygen absorption and utilization, visibly healthy appearance, normalization of the liver function (laboratory values) in the region of the tumor hyperthermia with the body temperature otherwise being normal, typical sweating, return of nerve function in the case of nerves which had failed due to the tumor, reduction of the inflammatory reaction in the vicinity of the tumors; after involuntary placebo test (20 days), during which time there was an increased growth in the size of the metastasis in the lungs and severe dyspnea, after another larger dose of the agent, excretion in the urine of grams of triple phosphate, whereupon there was again a clear improvement in the respiration and in the general condition.

The individual phases of the diagnosis and treatment can be described as follows in one individual case:

1st Phase

The patient, H. A., was a 67 years old male. In January of 1981 "carcinoma of the retrolingual tonsillary region" was diagnosed. The histological findings were: squamous cell carcinoma, moderately strongly keratinizing and moderately differentiated. The clinical stage was $T_3N_2M_0$. A few days later, a typical operation was performed with tumor resection, partial removal of the lower jaw bone and radical "neck dissection" on the left side.

Resection did not reach sound tissue everywhere. Thereafter the patient received the typical radiation treatment with an average dose of a total of 60 Gy. One week after the end of the radiotherapy, there was bleeding from esophageal varices, grade IV, which was controlled conservatively. In February of 1982, an en-bloc-re-resection of a local tumor recidivism with submental lymph adenectomy was performed. The histological finding was the same. Thereupon, local x-radiation treatment was employed with a focal dose of 30 Gy.

In March 1982, because of a pronounced swelling of the rest of the tongue 50 ml of an adjuvant cocktail of 96% ethanol and highly pure acetaldehyde in a ratio of 1000 ml to 40 ml, diluted with 10 volumes of water was administered daily in an amount of 550 ml. Accompanying this, a low-glucose diet was maintained. This resulted in the desired relief. The leukocyte count—which had previously been between 3000 and 4000/µl—increased as a result of this treatment to 4000 to 5000/µl. Lymphocyte irritation cells (Rieder), lymphatic plasma cells and young monocytes were found in amount of up to 4% in the differential white blood count.

2nd Phase

In July, 1982 a tumor node of the size of a cherry could be palpated in the left submental region. The patient inhaled a suspension of liposomes with MDP each day for three weeks for purposs of immune stimulation. The leukocyte count increased to values of about 5000 per µl.

In the differential white blood count, the Rieder cells and the young monocytes increased to 6%. After these three weeks, the tumor node was removed. The histological findings showed significant macrophage suppuration in addition to the known carcinoma.

3rd Phase

After 14 days without treatment, tumor metastases of the size of a quali's egg were found for the first time in the monthly control x-ray of the lung. Liver metastases and an enlargement of the spleen were found sonographically. Thereupon cytostatic chemotherapy was immediately introduced for 5 days.

A second series, two months later, had to be interrupted after the first day of treatment because of life-threatening complications. Between and after the chemotherapy series, the above-mentioned adjuvant cocktail and immune-stimulating inhalations were administered intermittently.

4th Phase

Since February, 1983 the cocktail, the low-glucose diet and an inhalation of liposomes which contained a different derivative of MDP were used each day. The leukocyte count increased to an average of 6000/µl. The differential white blood count showed Rieder lymphocytes and young monocytes in an amount of 15%. These two types of cells decreased in number when the leukocyte count increased to 9000/µl and increased with the leukocyte count was at 4000/µl.

A daily rate of Rieder lymphocytes and young monocytes of 900/µl blood was found. A plum-size metastasis, which had developed in the horizontal scar on the left neck in January of 1983, disappeared in April 1983 without the formation of additional scars. The pus contained macrophages. The same was noted in the case of another skin metastasis and a lymph node metastasis. The round shadows in the lung x-ray pictures becamse continuously larger from February 1983 to the end of May 1983.

During the same period of time, the patient stated that he was free of pain and felt well. Because of the amount of macrophages continuously produced, the increase in size of the lung metastases without the formation of new metastases led to the idea that the growth could be due in part to the formation by macrophages of a capsule around the metastases.

On May 3, 1983, the patient was subjected to a scintigraphic test after inhalation of liposomes, tagged with 99 m Tc. The aerosol contained 50 mCi. The patient was scanned with a nuclear Chicago gamma camera which was provided with a high resolution 140 KeV parallel collimator and a Simis 3-data system (Informatek, Birmingham, Ala., USA). Ten second dynamic scannings were carried out continuously for one hour.

From the resultant pictures, the localization of the radioactivity was determined for the region of interest. An hour after the application of the 99 m Tc liposomes by aerosol, 1.5% of the radioactivity was found in the lung. The balance was found in the upper respiratory tract and in the larynx. Computer substraction of the background activity permits a clear visualization of the metastases. The liposome trace is present predominantly in the pre-bronchial region. It shows an asymmetry of distribution which corresponds very precisely to the x-ray pictures.

At this time, about 5% of the lung radioactivity was found in the circulation, as shown by the gamma camera scanning of the legs of the patient. Four hours after the inhalation of the 99 m Tc liposome suspension, increased radioactivity was found in the circulation and in the digestive tract. This may be due to the dissociation of the 99 m Tc and the binding of this tracer to molecles which are able to pass through capillary walls. At no time was a concentration of radioactivity found in the liver. In June of 1983, liver metastases could not be found sonographically.

5th Phase

In September of 1983 there was a pronounced attack of cirrhosis of the liver which had already been known prior to the carcinosis. After a 14-day interruption of the treatment as a result thereof, a liver metastasis of somewhat less than 3 cm in diameter was found sonographically. In the x-ray control picture of the lung, a few new metastases of bean size were found alongside of air-filled structures in old lung metastases which were in the course of breakdown.

In one case of a female patient with a melanosarcoma who had been treated with the same combination as the above patient since February of 1983, the scintigraphic test showed a known bean-size melanoma node in the musculature of the left side of the neck, another known melanoma node in an adenoma of the right thyroid and three melanosarcoma nodes of the size approximately of a barley corn, two thereof in the region of the thorax wall musculature and one in the prevertebral fatty tissue in the center of the thorax. By the treatment, local metastases of the melanoma on the left thigh, inguinal lymph node metastases on both sides and para-aortal lymph node metastases had in this case been reduced.

Further in accordance with the present invention, a kit is provided for use in diagnosis and/or therapy. The kit contains two reagents, the first being the aldehyde of Formula I and the second being the liposome, each being in combination with a pharmaceutically acceptable carrier. The reagent containing the aldehyde of Formula I can, and preferably does, also contain the alcohol of Formula II. It will be appreciated that when the aldehyde is prepared by the procedure of irradiating an alcohol as described above, the resulting reagent will also contain peroxide. These reagents will be in a form appropriate for oral and/or parenteral administration. The kit can further contain a third reagent for the purpose of increasing deoxygenation such as inositol hexaphosphate, -pentaphosphate, -tetraphosphate or -triphosphate or glycerine di- or tri-phosphate, preferably incorporated into erythrocites, together with a pharmaceutically acceptable carrier therefor.

Further in accordance with the present invention, the composition may comprise an aldehyde derivative or a chemical compound metabolisable to said aldehyde. Said aldehyde derivative metabolisable to said aldehyde is a compound in which urea is bound to an aldehyde of formula I and/or a compound deriving from urea and/or a compound deriving from urea wherein the oxygen is substituted by sulfur and/or a chemical substituent of the same effect and/or a compound wherein one or both $NH_2$ groups being replaced by a $—S—(CH_2)_nH$ group in which n is 0 to 25, preferably 0 to 4, or a group of the same fate in metabolism or a compound which can be regarded as a combination of the aldehyde of formula I with $NH_3$ or its derivative, amino acids, amino sugars, sugars, 1,3-dioxolanes, 1,3-dioxanes, 1,3-dithiolanes, 1,3-dithianes, imidazolidines, oxazolidines, thiazolidines and compounds of aldehydes of formula I with vitamines, purinebases and/or pyrimidinebases and/or nucleosides and/or nucleotides and/or their derivatives which through metabolism set free an aldehyde of formula I, semiacetales and/or acetales of the aldehyde of formula I with alcohols of the formula $H(CH_2)_nOH$ in which n is 1 to 25, preferably 0 to 4, and/or their derivatives which through metabolism set free an aldehyde of formula I.

In another preferred embodiment according to this invention, the chemical compound metabolisable to said aldehyde is a compound of the formula $R''-S-R'''$ in which $R''$ is a straight-chain or branched hydrocarbon group having 1 to 4 carbon atoms and in which $R'''$ is H or the same as $R''$, or a compound of the formula $R''-S-S-R''$ wherein $R''$ has the meaning given above.

According to a preferred embodiment of this invention, the composition comprises the above named aldehyde derivatives metabolisable to said aldehyde or the above named chemical compounds metabolisable to said aldehyde together with the alcohol of formula II $R'CH_2OH$ in which $R'$ is a hydrogen atom or a straight-chain or branched hydrocarbon group having 1 to 4 carbon atoms. It is especially preferred that in such compositions R and $R'$ have the same number of carbon atoms. Preferred compositions comprising an aldehyde derivative or a chemical compound metabolisable to said aldehyde which produce formaldehyde by metabolism, comprise methanol; such which produce acetaldehyde, comprise ethanol; such which produce n-propionaldehyde, comprise n-propanol; such which produce isopropionaldehyde comprise isopropanol; such which produce n-butyraldehyde, comprise n-butanol; such which produce isobutyraldehyde, comprise isobutanol; such which produce tert.-butyraldehyde, comprise tert.-butanol; such which produce n-valeraldehyde, comprise n-pentanol or mixtures thereof.

In a further preferred embodiment, the above described compositions comprise hydrogen peroxyde or another peroxyde.

In the method for facilitating the transport of liposomes according to this invention, the aldehyde derivative or the chemical compound metabolisable to said aldehyde can be the same type of compounds as outlined in connection with the composition according to this invention. The same applies for the kit according to this invention.

The kit according to this invention can comprise two or, as outlined before, three reagents.

The first reagent of the kit being the aldehyde of formula I and/or an aldehyde derivative or a chemical compound metabolisable to said aldehyde.

In a preferred embodiment of the kit, said aldehyde derivative metabolisable to said aldehyde is a compound in which urea is bound to an aldehyde of formula I and/or a compound deriving from urea and/or a compound deriving from urea wherein the oxygen is substituted by sulfur and/or a chemical substituent of the same effect and/or a compound wherein one or both $NH_2$ groups being replaced by a —S—$(CH_2)_n$H group in which n is 0–25, preferably 0–4, or a group of the same fate in metabolism or a compound which can be regarded as a combination of the aldehyde of formula I with $NH_3$ or its derivatives, amino acids, amino sugars, sugars, 1,3-dioxolanes, 1,3-dioxanes, 1,3-dithiolanes, 1,3-dithianes, imidazolidines, oxazolidines, thiazolidines and compounds of aldehydes of formula I with vitamines, purinebases and/or pyrimidinebases and/or nucleosides and/or nucleotides and/or their derivatives which through metabolism set free an aldehyde of formula I, semi-acetales and/or acetales of the aldehyde of formula I with alcohols of the formula $H(CH_2)_nOH$ in which n is 1 to 25, preferably 0 to 4, and/or their derivatives which through metabolism set free an aldehyde of formula I.

In another preferred kit according to this invention, the chemical compound metabolisable to said aldehyde is a compound of the formula R'-S-R''' in which R'' is a straight-chain or branched hydrocarbon group having 1 to 4 carbon atoms and in which R''' is H or the same as R'', or a compound of the formula R''-S-S-R'' wherein R'' has the meaning given above. It is especially preferred that the reagent containing the aldehyde derivative or a chemical compound metabolisable to said aldehyde contains also the alcohol of formula II.

What is claimed is:

1. A method of facilitating the transport of liposomes through cellular walls comprising the step of administering to a mammal a liposome cellular wall transport facilitating amount of an aldehyde of formula I $$RCHO \qquad (I)$$

in which R is a hydrogen atom or a straight-chain or branched hydrocarbon group having 1 to 4 carbon atoms or an aldehyde derivative or a chemical compound metabolisable to said aldehyde in combination with an alcohol of formula II $$R'CH_2OH \qquad (II)$$

in which R' is a hydrogen atom or a straight-chain or branched hydrocarbon group having 1 to 4 carbon atoms and liposomes.

2. A method according to claim 1 wherein said aldehyde derivative metabolisable to said aldehyde is a compound in which urea is bound to an aldehyde of formula I or a compound deriving from urea or a compound deriving from urea wherein the oxygen is substituted by sulfur or a chemical substituent of the same effect or a compound wherein one or both $NH_2$ groups being replaced by a —S—$(CH_2)_m$H group in which m is 0–25, or a group of the same fate in metabolism or a compound which can be regarded as a combination of the aldehyde of formula I with $NH_3$ or its derivatives, amino acids, amino sugars, sugars, 1,3-dioxolanes, 1,3-dioxanes, 1,3-dithiolanes, 1,3-dithianes, imidazolidines, oxazolidines, thiazolidines and compounds of aldehydes of formula I with vitamines, purine-bases or pyrimidinbases or nucleosides or nucleotides or their derivatives which through metabolism set free an aldehyde of formula I, semi-acetales or acetales of the aldehyde of formula I with alcohls of the formula $H(CH_2)_nOH$ in which n is 1 to 25 or their derivatives which through metabolism set free an aldehyde of formula I or mixtures thereof.

3. A method according to claim 1 wherein said chemical compound metabolisable to said aldehyde is a compound of the formula R''-S-R''' in which R'' is a straight-chain or branched hydrocarbon group having 1 to 4 carbon atoms and in which R''' is H or the same as R'', or a compound of the formula R''-S-S-R'' wherein R'' has the meaning given above.

4. A method according to claim 1 wherein the aldehyde and the alcohol are employed in combination with a peroxide.

5. A method according to claim 4 wherein R and R' are methyl.

6. A method according to claim 5 wherein 11 to 40 g of aldehyde per 1,000 g of alcohol is employed.

7. A method according to claim 6 wherein 15 to 30 g of aldehyde per 1,000 g of alcohol is employed.

8. A method according to claim 1 wherein a liposome is thereafter administered.

9. A method according to claim 8 wherein the liposome carries a dyestuff, a radioactive tracer, a radioactive tracer and a dyestuff, a cytostatic, a radioactive radiator, a radioactive radiator and/or an immune modulator, or a cytostatic and a radioactive radiator.

10. A method according to claim 1 wherein the administration of aldehyde and alcohol is oral or parenteral.

11. A method according to claim 2 wherein the administration of the liposome is oral or parenteral.

12. A method according to claim 1 wherein the aldehyde is administered orally and the liposome is administered by inhalation.

13. A method according to claim 1 wherein the liposome is administered with an agent adapted to increase the deoxygenation in the region of a malignant tumor.

14. A method according to claim 13 wherein the agent for increasing the deoxygenation is an inositol phosphate or glycerine phosphate.

15. A method according to claim 2 in which m is 0–4 and in which n in the formula $H(CH_2)_nOH$ is 1–4.

16. A kit comprising a container of a first reagent and a container of a second reagent, said first reagent comprising a liposome cellular wall transport facilitating amount of an aldehyde of formula I $$RCHO \qquad (I)$$

in which R is a hydrogen atom or a straight-chain or branched hydrocarbon group having 1 to 4 carbon atoms or an aldehyde derivative or a chemical compound metabolisable to said aldehyde in combination with an alcohol of formula II $$R'CH_2OH \qquad (II)$$

in which R' is a hydrogen atom or a straight-chain or branched hydrocarbon group having 1 to 4 carbon atoms, and said second reagent comprising a pharmaceutically acceptable carrier and a liposome.

17. A kit according to claim 16 wherein said first reagent further comprises a peroxide.

18. A kit according to claim 17 in which said peroxide is hydrogen peroxide.

19. A kit according to claim 16, further comprising a container of a third reagent which comprises a pharmaceutically acceptable carrier and an agent adapted to increase the deoxygenation in the region of a malignant tumor.

20. A kit according to claim 16 wherein said aldehyde derivative metabolisable to said aldehyde is a compound in which urea is bound to an aldehyde of formula I or a compound deriving from urea or a compound deriving from urea wherein the oxygen is substituted by sulfur or a chemical substituent of the same effect or a compound wherein one or both $NH_2$ groups being replaced by a $-S-(CH_2)_mH$ group in which m is 0–25 or a group of the same fate in metabolism or a compound which can be regarded as a combination of the aldehyde of formula I with $NH_3$ or its derivatives, amino acids, amino sugars, sugars, 1,3-dioxolanes, 1,3-dioxanes, 1,3-dithiolanes, 1,3-dithianes, imidazolidines, oxazolidines, thiazolidines and compounds of aldehydes of formula I with vitamines, purinebases or pyrimidinebases or nucleosides or nucleotides or their derivatives which through metabolism set free an aldehyde of formula I, semi-acetales or acetales of the aldehyde of formula I with alcohols of the formula $H(CH_2)_nOH$ in which n is 1 to 25 or their derivatives which through metabolism set free an aldehyde of formula I, or mixtures thereof.

21. A kit according to claim 16 wherein said chemical compound metabolisable to said aldehyde is a compound of the formula R"-S-R'" in which R" is a straight-chain or branched hydrocarbon group having 1 to 4 carbon atoms and in which R'" is H or the same as R", or a compound of the formula R"-S-S-R" wherein R" has the meaning given above.

22. A kit according to claim 16 wherein R and R' have the same number of carbon atoms.

23. A kit according to claim 22 wherein the aldehyde and the alcohol are formaldehyde/methanol, acetaldehyde/ethanol, n-propionaldehyde/n-propanol, isopropionaldehyde/isopropanol, n-butyraldehyde/n-butanol, isobutyraldehyde/isobutanol, tert.-butyraldehyde/tert.-butanol, n-valeraldehyde/n-pentanol or mixtures thereof.

24. A kit according to claim 23 containing 11 to 40 g of aldehyde per 1,000 g of alcohol.

25. A kit according to claim 24 containing 15 to 30 g of aldehyde per 1,000 g of alcohol.

26. A kit according to claim 16 wherein the aldehyde is acetaldehyde and the alcohol is ethanol.

* * * * *